(12) United States Patent
Stormont et al.

(10) Patent No.: US 9,354,287 B2
(45) Date of Patent: May 31, 2016

(54) SYSTEM AND APPARATUS FOR RECEIVING MAGNETIC RESONANCE (MR) SIGNALS FROM AN IMAGING SUBJECT

(75) Inventors: Robert S. Stormont, Hartland, WI (US); Dashen Chu, Hartland, WI (US)

(73) Assignee: General Electric Company, Schenectady, NY (US)

( * ) Notice: Subject to any disclaimer, the term of this patent is extended or adjusted under 35 U.S.C. 154(b) by 2671 days.

(21) Appl. No.: 11/851,961

(22) Filed: Sep. 7, 2007

(65) Prior Publication Data

US 2009/0067697 A1 Mar. 12, 2009

(51) Int. Cl.
*A61B 5/05* (2006.01)
*G01R 33/36* (2006.01)
*A61B 5/055* (2006.01)

(52) U.S. Cl.
CPC .............. *G01R 33/365* (2013.01); *A61B 5/055* (2013.01); *G01R 33/3621* (2013.01)

(58) Field of Classification Search
USPC .................. 600/407, 409, 410; 324/306, 307
See application file for complete search history.

(56) References Cited

U.S. PATENT DOCUMENTS

| | | | | |
|---|---|---|---|---|
| 4,151,395 A | * | 4/1979 | Kushner et al. | 219/125.12 |
| 5,298,861 A | * | 3/1994 | Sugimoto | 324/306 |
| 5,933,040 A | * | 8/1999 | Rokhsaz et al. | 327/306 |
| 6,313,630 B1 | * | 11/2001 | Ganin et al. | 324/312 |
| 2002/0032004 A1 | * | 3/2002 | Widrow | 455/22 |
| 2003/0011880 A1 | * | 1/2003 | Kim et al. | 359/341.41 |
| 2008/0246475 A1 | * | 10/2008 | Adachi | 324/307 |

* cited by examiner

*Primary Examiner* — Joel F Brutus
(74) *Attorney, Agent, or Firm* — Dean D. Small; The Small Patent Law Group, LLC

(57) ABSTRACT

An apparatus for receiving magnetic resonance (MR) signals emitted by an imaging subject includes a receiver coil configured to detect the MR signals and a frequency translating preamplifier coupled to the receiver coil. The frequency translating preamplifier is configured to amplify the MR signals and to convert a frequency of the MR signals to an intermediate frequency. The frequency translating preamplifier may include an amplifier having a predefined gain, a frequency filter configured to filter at least one predetermined frequency and a mixer configured to convert the frequency of the MR signals to the intermediate frequency.

19 Claims, 4 Drawing Sheets

SYSTEM AND APPARATUS FOR RECEIVING MAGNETIC RESONANCE (MR) SIGNALS FROM AN IMAGING SUBJECT

FIELD OF THE INVENTION

The present invention relates generally to magnetic resonance imaging (MRI) systems and in particular to a frequency translating preamplifier for converting the frequency of MR signals received from an imaging subject.

BACKGROUND OF THE INVENTION

Magnetic resonance imaging (MRI) is a medical imaging modality that can create images of the inside of a human body without using x-rays or other ionizing radiation. MRI uses a powerful magnet to create a strong, uniform, static magnetic field (i.e., the "main magnetic field"). When a human body, or part of a human body, is placed in the main magnetic field, the nuclear spins that are associated with the hydrogen nuclei in tissue water become polarized. This means that the magnetic moments that are associated with these spins become preferentially aligned along the direction of the main magnetic field, resulting in a small net tissue magnetization along that axis (the "z axis," by convention). An MRI system also comprises components called gradient coils that produce smaller amplitude, spatially varying magnetic fields when a current is applied to them. Typically, gradient coils are designed to produce a magnetic field component that is aligned along the z axis and that varies linearly in amplitude with position along one of the x, y or z axes. The effect of a gradient coil is to create a small ramp on the magnetic field strength and concomitantly on the resonant frequency of the nuclear spins, along a single axis. Three gradient coils with orthogonal axes are used to "spatially encode" the MR signal by creating a signature resonance frequency at each location in the body. Radio frequency (RF) coils are used to create pulses of RF energy at or near the resonance frequency of the hydrogen nuclei. The RF coils are used to add energy to the nuclear spin system in a controlled fashion. As the nuclear spins then relax back to their rest energy state, they give up energy in the form of an RF signal. The RF signal is detected by an RF receiver coil or coils and is transformed into an image using a computer and known reconstruction algorithms.

The amplitude of the signals detected by the RF receiver coil(s) are typically small. An RF receiver coil may be connected to a preamplifier that is used to amplify the signals detected by the RF receiver coil prior to further signal processing. In an MRI system with a plurality of RF receiver coils, a preamplifier may be provided for each RF receiver coil. Preamplifiers reduce loop to loop coupling and improve the system noise figure. A preamplifier, however, can radiate from its output interface and create an oscillator. A low loss, highly shielded output cable and connector may be used to minimize coupling and loss, however, such cables and connectors may not be size or cost efficient, in particular, in a system with a plurality of RF receiver coils. Therefore, there is a need for a system and apparatus to reduce or eliminate oscillation created by the preamplifiers.

BRIEF DESCRIPTION OF THE INVENTION

In accordance with an embodiment, an apparatus for receiving magnetic resonance (MR) signals emitted by an imaging subject includes a receiver coil configured to detect the MR signals and a frequency translating preamplifier coupled to the receiver coil and configured to amplify the MR signals and to convert a frequency of the MR signals to an intermediate frequency.

In accordance with another embodiment, a system for receiving magnetic resonance (MR) signals emitted by an imaging subject includes at least one receiver coil configured to detect the MR signals, at least one frequency translating preamplifier coupled to the at least one receiver coil and configured to amplify the MR signals and to convert a frequency of the MR signals to an intermediate frequency and a receiver coupled to the at least one frequency translating preamplifier and configured to process the amplified MR signals.

In accordance with another embodiment, a frequency translating preamplifier for a receiver coil in a magnetic resonance imaging (MRI) system includes an amplifier having a predetermined gain and configured to receive at least one magnetic resonance (MR) signal from the receiver coil and to generate an amplified MR signal, a frequency filter coupled to the amplifier and configured to filter at least one predetermined frequency and a mixer coupled to the frequency filter and configured to convert the frequency of the amplified MR signal to an intermediate frequency.

BRIEF DESCRIPTION OF THE DRAWINGS

The invention will become more fully understood from the following detailed description, taken in conjunction with the accompanying drawings, in which.

DETAILED DESCRIPTION

Figure 1:
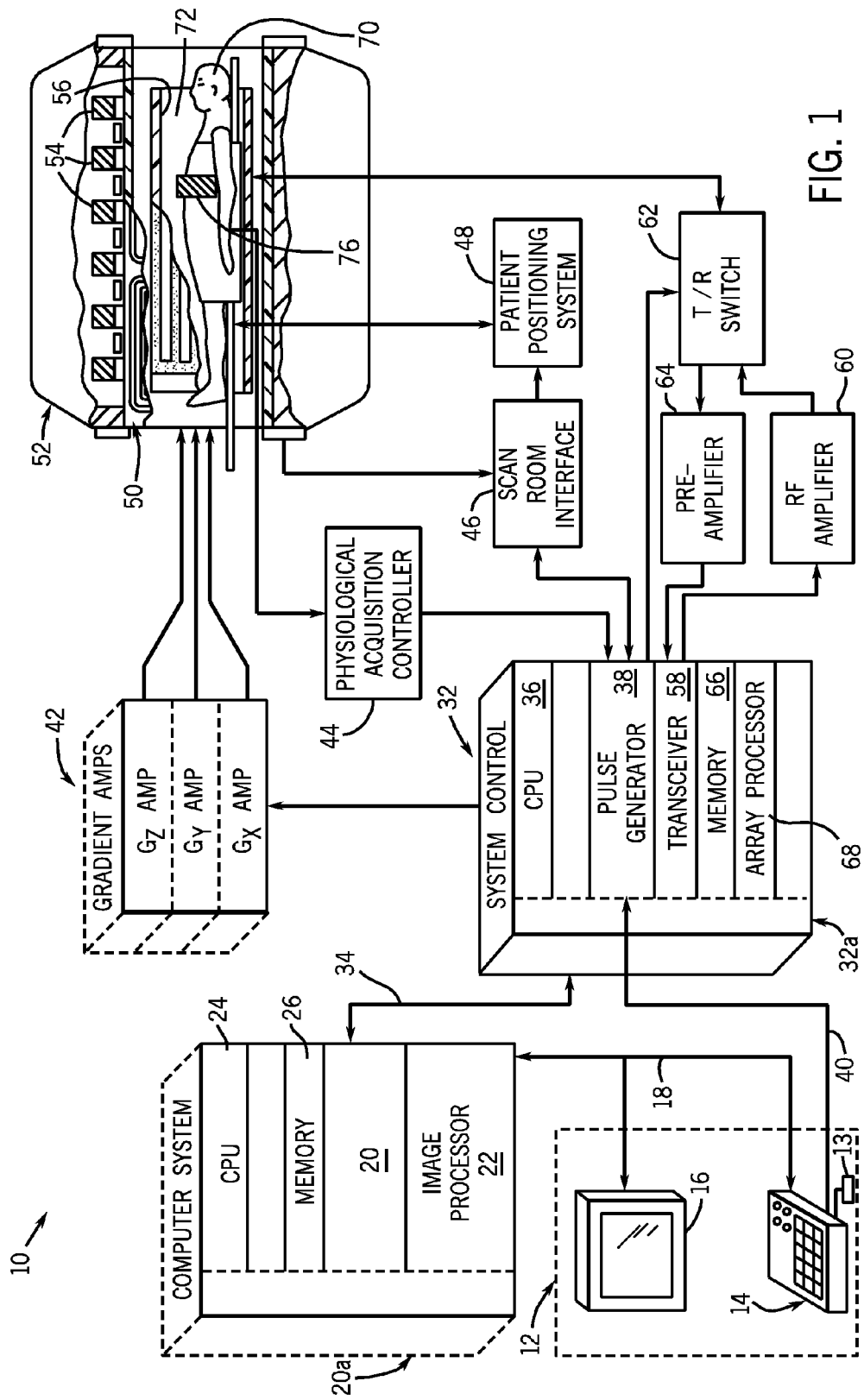
FIG. 1 is a schematic block diagram of an exemplary magnetic resonance imaging system in accordance with an embodiment.

FIG. 1 is a schematic block diagram of an exemplary magnetic resonance imaging system in accordance with an embodiment. The operation of MRI system 10 is controlled from an operator console 12 that includes a keyboard or other input device 13, a control panel 14, and a display 16. The console 12 communicates through a link 18 with a computer system 20 and provides an interface for an operator to prescribe MRI scans, display resultant images, perform image processing on the images, and archive data and images. The computer system 20 includes a number of modules that communicate with each other through electrical and/or data connections, for example, such as are provided by using a backplane 20a. Data connections may be direct wired links or may be fiber optic connections or wireless communication links or the like. The modules of the computer system 20 include an image processor module 22, a CPU module 24 and a memory module 26 which may include a frame buffer for storing image data arrays. In an alternative embodiment, the image processor module 22 may be replaced by image processing functionality on the CPU module 24. The computer system 20 is linked to archival media devices, permanent or back-up memory storage or a network. Computer system 20 may also communicate with a separate system control computer 32 through a link 34. The input device 13 can include a mouse, joystick, keyboard, track ball, touch activated screen, light wand, voice control, or any similar or equivalent input device, and may be used for interactive geometry prescription.

The system control computer 32 includes a set of modules in communication with each other via electrical and/or data connections 32a. Data connections 32a may be direct wired links, or may be fiber optic connections or wireless communication links or the like. In alternative embodiments, the modules of computer system 20 and system control computer 32 may be implemented on the same computer systems or a plurality of computer systems. The modules of system control computer 32 include a CPU module 36 and a pulse generator module 38 that connects to the operator console 12 through a communications link 40. The pulse generator module 38 may alternatively be integrated into the scanner equipment (e.g., magnet assembly 52). It is through link 40 that the system control computer 32 receives commands from the operator to indicate the scan sequence that is to be performed. The pulse generator module 38 operates the system components that play out (i.e., perform) the desired pulse sequence by sending instructions, commands and/or requests (e.g., radio frequency (RF) waveforms) describing the timing, strength and shape of the RF pulses and pulse sequences to be produced and the timing and length of the data acquisition window. The pulse generator module 38 connects to a gradient amplifier system 42 and produces data called gradient waveforms which control the timing and shape of the gradient pulses that are to be used during the scan. The pulse generator module 38 may also receive patient data from a physiological acquisition controller 44 that receives signals from a number of different sensors connected to the patient, such as ECG signals from electrodes attached to the patient. The pulse generator module 38 connects to a scan room interface circuit 46 that receives signals from various sensors associated with the condition of the patient and the magnet system. It is also through the scan room interface circuit 46 that a patient positioning system 48 receives commands to move the patient table to the desired position for the scan.

The gradient waveforms produced by the pulse generator module 38 are applied to gradient amplifier system 42 which is comprised of $G_x$, $G_y$ and $G_z$ amplifiers. Each gradient amplifier excites a corresponding physical gradient coil in a gradient coil assembly generally designated 50 to produce the magnetic field gradient pulses used for spatially encoding acquired signals. The gradient coil assembly 50 forms part of a magnet assembly 52 that includes a polarizing magnet 54 and may include a whole-body RF coil 56, surface or parallel imaging coils 76 or both. The coils 56, 76 of the RF coil assembly may be configured for both transmitting and receiving or for transmit-only or receive-only. A patient or imaging subject 70 may be positioned within a cylindrical patient imaging volume 72 of the magnet assembly 52. A transceiver module 58 in the system control computer 32 produces pulses that are amplified by an RF amplifier 60 and coupled to the RF coils 56, 76 by a transmit/receive switch 62. The resulting signals emitted by the excited nuclei in the patient may be sensed by the same RF coil 56 and coupled through the transmit/receive switch 62 to a preamplifier 64. Alternatively, the signals emitted by the excited nuclei may be sensed by separate receive coils such as parallel coils or surface coils 76. The amplified MR signals are demodulated, filtered and digitized in the receiver section of the transceiver 58. The transmit/receive switch 62 is controlled by a signal from the pulse generator module 38 to electrically connect the RF amplifier 60 to the RF coil 56 during the transmit mode and to connect the preamplifier 64 to the RF coil 56 during the receive mode. The transmit/receive switch 62 can also enable a separate RF coil (for example, a parallel or surface coil 76) to be used in either the transmit or receive mode.

The MR signals sensed by the RF coil 56 are digitized by the transceiver module 58 and transferred to a memory module 66 in the system control computer 32. Typically, frames of data corresponding to MR signals are stored temporarily in the memory module 66 until they are subsequently transformed to create images. An array processor 68 uses a known transformation method, most commonly a Fourier transform, to create images from the MR signals. These images are communicated through the link 34 to the computer system 20 where it is stored in memory. In response to commands received from the operator console 12, this image data may be archived in long-term storage or it may be further processed by the image processor 22 and conveyed to the operator console 12 and presented on display 16.

Figure 2:
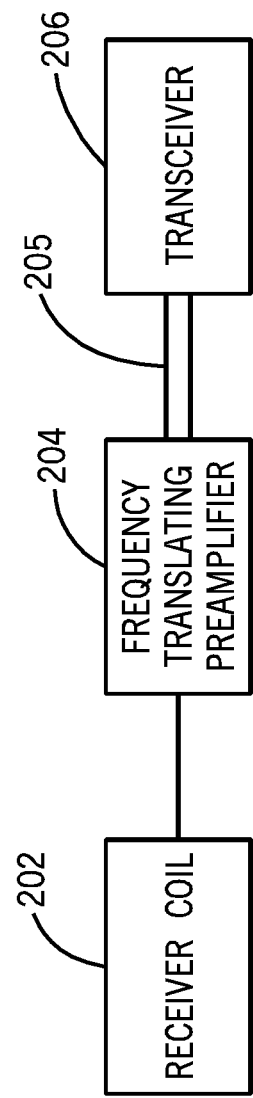
FIG. 2 is a simplified schematic block diagram of a receive path of an MRI system in accordance with an embodiment.

FIG. 2 is a simplified schematic block diagram of a receive path for a MRI system in accordance with an embodiment. Receive path 200 is compatible with the above-described MRI system of FIG. 1 or any similar or equivalent system for obtaining MR images. Receive path 200 includes an RF receiver coil 202, a frequency translating preamplifier 204 and a transceiver 206. Various other elements such as a transmit/receive switch, etc. are omitted from FIG. 2 for clarity. RF receiver coil 202 may be, for example, a whole-body RF coil, a surface coil, a head coil, a coil in an array of coils, etc. and is configured to detect signals emitted from an imaging subject in response to magnetic fields and RF pulses applied to the imaging subject. RF receiver coil 202 is coupled to and is in signal communication with a frequency translating preamplifier 204. The signals detected by receiver coil 202 are provided to the frequency translating preamplifier 204 that is configured to amplify the signals and to convert the frequency of the amplified signals to an intermediate frequency as described in more detail below with respect to FIG. 3. The intermediate frequency is a different frequency than the frequency of the acquired signals. Accordingly, the output of the frequency translating preamplifier 204 will not radiate at the MR frequency and an oscillation will not occur.

In one embodiment, the intermediate frequency is a frequency lower than the acquired MR signal frequency. In another embodiment, the intermediate frequency is a frequency higher than the acquired MR signal frequency. Frequency translating preamplifier 204 is coupled to and is in signal communication with a transceiver 206 via an interface or connector 205. The amplified signals are transmitted from the frequency translating preamplifier 204 to, for example, a receiver section of a transceiver 206 for further processing (e.g., demodulation, filtering, digitization, further amplification, etc.). In an embodiment where the intermediate frequency is lower than the acquired MR signal frequency, interface or connector 205 is a low frequency compatible interface or connector including, but not limited to, a twisted pair cable. In an embodiment where the intermediate frequency is higher than the acquired MR signal frequency, interface or connector 205 is a high frequency compatible interface or connector including, but not limited to, a coaxial cable.

Figure 3:
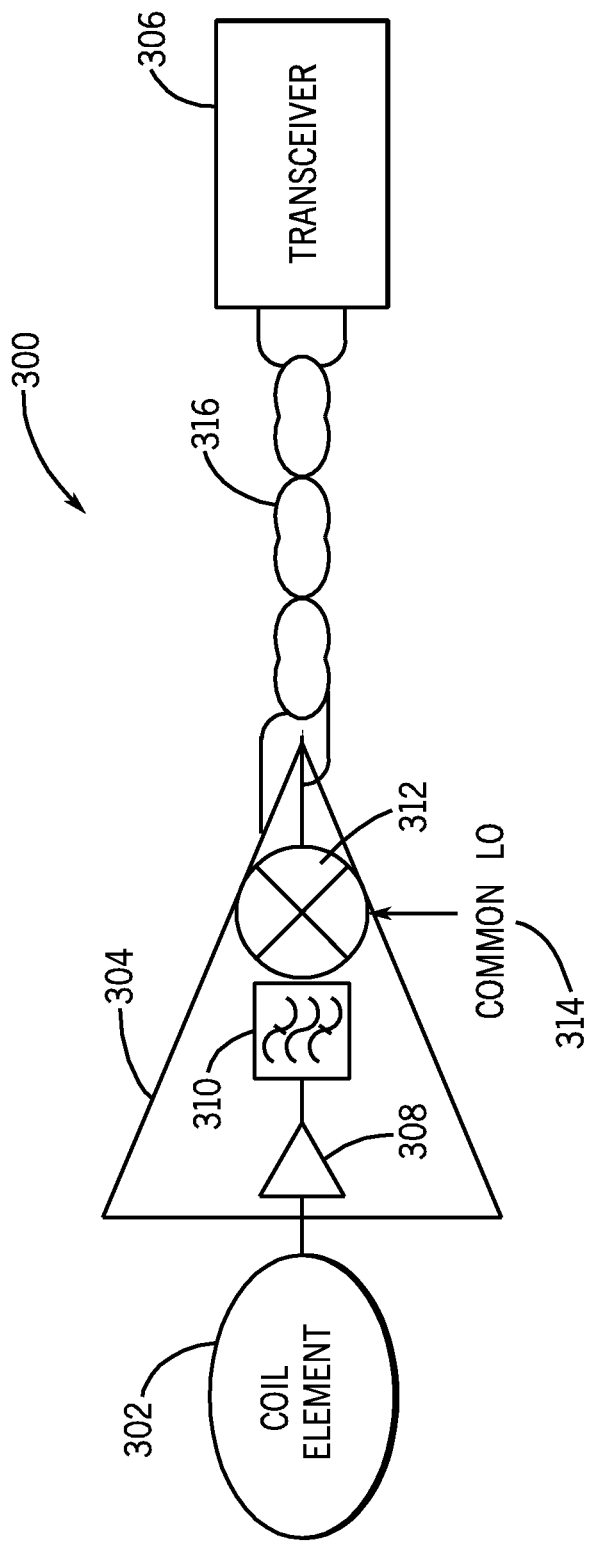
FIG. 3 is a simplified schematic block diagram of a receive path including details of a frequency translating preamplifier in accordance with an embodiment.

As mentioned, a frequency translating preamplifier 204 is used to amplify the signals received by the receiver coil 202 and to convert the frequency of the amplified signals to an intermediate frequency. FIG. 3 is a simplified schematic block diagram of a receive path including details of a frequency translating preamplifier in accordance with an embodiment. Receive path 300 includes, among other elements, an RF receiver coil element 302, a frequency translating preamplifier 304, an interface or connector 316 and a transceiver 306. Various other elements such as a transmit/ receive switch, etc. are omitted from FIG. 3 for clarity. As mentioned above with respect to FIG. 2, RF receiver coil 302 may be, for example, a whole body RF coil, a surface coil, a head coil, a coil in an array of coils, etc. Frequency translating preamplifier 304 includes an amplifier 308, a frequency filter 310 and a mixer 312. A local oscillator (LO) signal 314 having a predetermined frequency is provided to mixer 310.

Signals acquired or sensed by the receiver coil element 302 are transmitted to the frequency translating preamplifier 304. The signals are amplified by amplifier 308 using a predefined gain. In one embodiment, amplifier 308 is a low noise, high gain amplifier. The amplified signals are then provided to a frequency filter 310 to filter out signals at unwanted frequencies and to allow signals at a predetermined frequency, frequencies or frequency band to pass through. Mixer 312 is then used to translate the frequency of the amplified MR signals to an intermediate frequency (IF) based on the frequency of the common local oscillator signal 314. The intermediate frequency is a different frequency than the frequency of the acquired signals. Accordingly, the output of the frequency translating preamplifier 304 will not radiate at the MR frequency and an oscillation will not occur. In one embodiment, the intermediate frequency is a frequency lower than the MR signal frequency. In this embodiment, shown in FIG. 3, the output of mixer 312 (and of the frequency translating preamplifier 304) is provided to transceiver 306 via a low frequency compatible interface or connector 316 including, but not limited to, a twisted pair cable. A low frequency compatible interface may be a less complex and less expensive interface. The configuration of the frequency translating preamplifier 304 may allow the use of high gain amplifiers (or preamplifiers) with unrestricted placement which can result in a higher signal-to-noise ratio (SNR). As mentioned above with respect to FIG. 2, in an alternative embodiment, the intermediate frequency is a frequency higher than the MR signal frequency and the interface or connector 205 (shown in FIG. 2) is a high frequency compatible interface.

Figure 4:
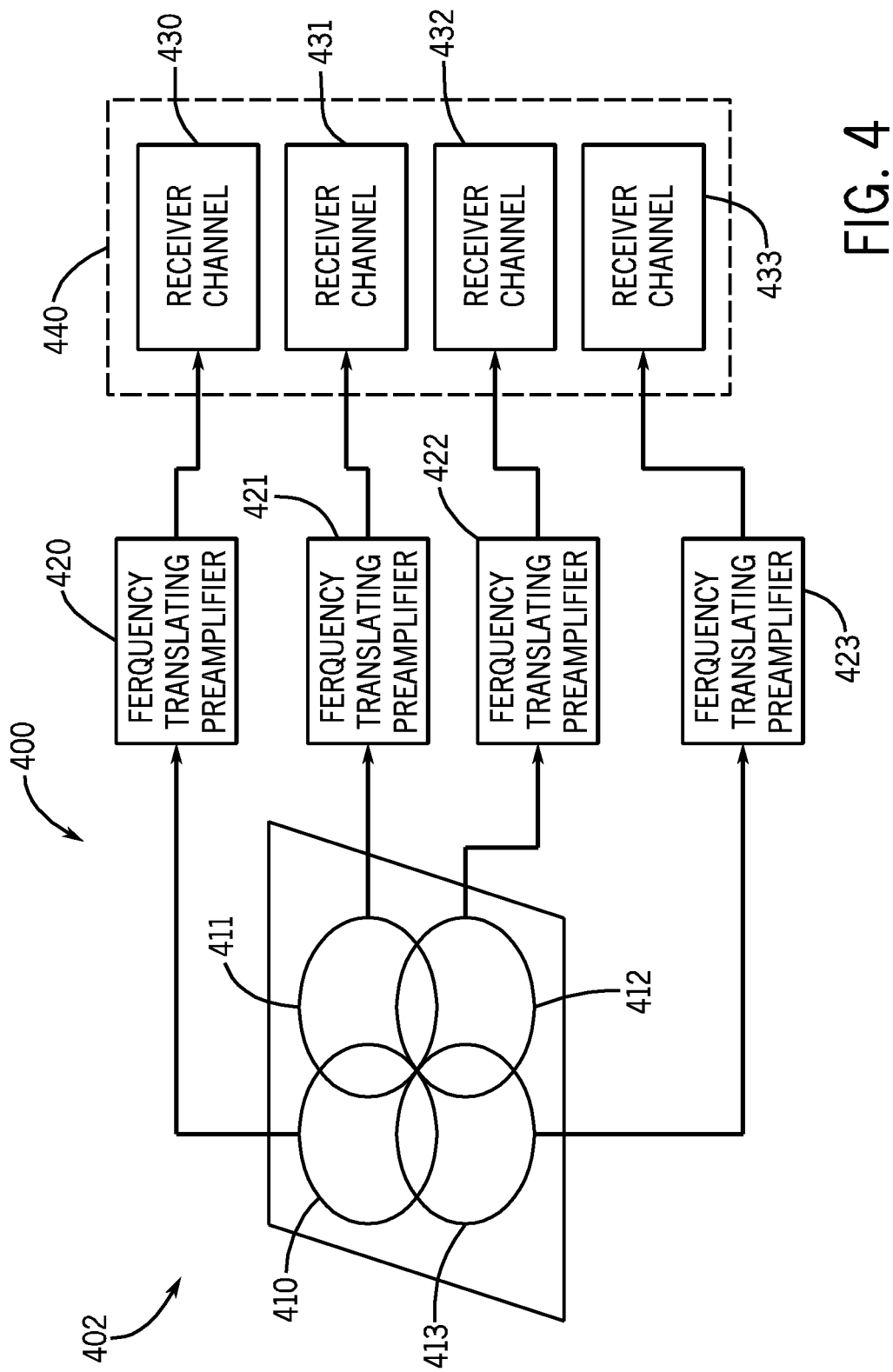
FIG. 4 is a simplified schematic block diagram of a receive path of an MRI system in accordance with an alternative embodiment.

In an alternative embodiment, receive path 300 may include a plurality or array of RF receiver coils. FIG. 4 is a simplified schematic block diagram of a receive path for an MRI system in accordance with an alternative embodiment. Receive path 400 is compatible with the above-described MRI system of FIG. 1 or any similar or equivalent system for obtaining MR images. Receive path 400 includes an array of RF receiver coils 402, in which each coil element separately detects MR signals. RF receiver coil arrays may include, but are not limited to, whole body arrays as well as partial body arrays such as head coil arrays, cardiac coil arrays, and spine coil arrays. An array of coil elements 402 is used to acquire MR data for a field-of-view (FOV) in an imaging subject and includes four separate coil elements 410, 411, 412 and 413. MR signals from each coil element 410, 411, 412, 413 are transmitted separately to a corresponding frequency translating preamplifier 420, 421, 422, 423, respectively. Frequency translating preamplifiers 420, 421, 422, 423 are each configured to amplify the signals received by the corresponding receiver coil 410, 411, 412, 413 and to convert the frequency of the amplified signals to an intermediate frequency. The amplified MR signals are transmitted separately to a corresponding receiver channel (or data acquisition channel) 430, 431, 432, 433, respectively, of a receiver 440 for further processing (e.g., demodulation, filtering, digitization, further amplification, etc.). The receiver 440 and receiver channels 430, 431, 432, 433 may be, for example, elements of a transceiver.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. The order and sequence of any process or method steps may be varied or re-sequenced according to alternative embodiments.

Many other changes and modifications may be made to the present invention without departing from the spirit thereof. The scope of these and other changes will become apparent from the appended claims.

We claim:

1. An apparatus for receiving magnetic resonance (MR) signals emitted by an imaging subject, the apparatus comprising:
   a receiver coil configured to detect the MR signals;
   a frequency translating preamplifier coupled to the receiver coil and configured to amplify the MR signals and to convert a frequency of the MR signals to an intermediate frequency; and
   a receiver coupled to an output of the frequency translating preamplifier and configured to receive the amplified and frequency converted MR signals.

2. An apparatus according to claim 1, wherein the intermediate frequency is different than the frequency of the MR signals.

3. An apparatus according to claim 2, wherein the intermediate frequency is lower than the frequency of the MR signals.

4. An apparatus according to claim 2, wherein the intermediate frequency is higher than the frequency of the MR signals.

5. An apparatus according to claim 1, wherein the frequency translating preamplifier comprises:
   an amplifier having a predefined gain;
   a frequency filter coupled to the amplifier and configured to filter at least one predetermined frequency; and
   a mixer coupled to the frequency filter and configured to convert the frequency of the MR signals to the intermediate frequency.

6. An apparatus according to claim 5, wherein the mixer is configured to convert the frequency of the MR signals to the intermediate frequency based on a local oscillator signal frequency.

7. An apparatus according to claim 5, wherein the amplifier is a low noise amplifier.

8. A system for receiving magnetic resonance (MR) signals emitted by an imaging subject, the system comprising:
   at least one receiver coil configured to detect the MR signals;
   at least one frequency translating preamplifier coupled to the at least one receiver coil and configured to amplify the MR signals and to convert a frequency of the MR signals to an intermediate frequency; and
   a receiver coupled to the at least one frequency translating preamplifier and configured to receive and process the amplified and frequency converted MR signals.

9. A system according to claim 8, wherein the at least one receiver coil is included in an array of receiver coils.

10. A system according to claim 8, wherein the receiver is a transceiver.

11. A system according to claim 8, further comprising a connector that couples the receiver to the at least one frequency translating preamplifier.

12. A system according to claim 11, wherein the connector is a low frequency compatible connector.

13. A system according to claim 12, wherein the connector is a twisted pair cable.

14. A system according to claim 8, wherein the at least one frequency translating preamplifier comprises:
   an amplifier having a predefined gain;
   a frequency filter coupled to the amplifier and configured to filter at least one predetermined frequency; and
   a mixer coupled to the frequency filter and configured to convert the frequency of the MR signals to the intermediate frequency.

15. A system according to claim 14, wherein the mixer is configured to convert the frequency of the MR signals to the intermediate frequency based on a local oscillator signal frequency.

16. A system according to claim 14, wherein the amplifier is a low noise amplifier.

17. A frequency translating preamplifier for a receiver coil in a magnetic resonance imaging (MRI) system, the frequency translating preamplifier comprising:
   an amplifier having a predetermined gain and configured to receive at least one magnetic resonance (MR) signal from the receiver coil and to generate an amplified MR signal;
   a frequency filter coupled to the amplifier and configured to filter at least one predetermined frequency; and
   a mixer coupled to the frequency filter and configured to convert the frequency of the amplified and filtered MR signal to an intermediate frequency.

18. A frequency translating preamplifier according to claim 17, wherein the mixer is configured to convert the frequency of the amplified MR signal to the intermediate frequency based on a local oscillator signal frequency.

19. A frequency translating preamplifier according to claim 17, wherein the amplifier is a low noise amplifier.

* * * * *